US011536728B2

(12) United States Patent
Ahn

(10) Patent No.: US 11,536,728 B2
(45) Date of Patent: Dec. 27, 2022

(54) METHOD FOR PRODUCING ANIMAL MODEL OF PRETERM BIRTH AND ANIMAL MODEL OF PRETERM BIRTH PRODUCED BY THE METHOD

(71) Applicant: KOREA UNIVERSITY RESEARCH AND BUSINESS FOUNDATION, Seoul (KR)

(72) Inventor: Ki Hoon Ahn, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 462 days.

(21) Appl. No.: 16/084,092

(22) PCT Filed: Apr. 18, 2017

(86) PCT No.: PCT/KR2017/004148
§ 371 (c)(1),
(2) Date: Sep. 11, 2018

(87) PCT Pub. No.: WO2017/191912
PCT Pub. Date: Nov. 9, 2017

(65) Prior Publication Data
US 2019/0086421 A1   Mar. 21, 2019

(30) Foreign Application Priority Data

May 6, 2016 (KR) .................. 10-2016-0055878
Apr. 13, 2017 (KR) .................. 10-2017-0047866

(51) Int. Cl.
| A01K 67/027 | (2006.01) |
| C12N 15/00 | (2006.01) |
| G01N 33/68 | (2006.01) |
| A61B 5/00 | (2006.01) |
| A61B 17/42 | (2006.01) |
| G09B 23/30 | (2006.01) |

(52) U.S. Cl.
CPC ......... *G01N 33/689* (2013.01); *A01K 67/027* (2013.01); *A61B 5/4343* (2013.01); *A61B 17/42* (2013.01); *A01K 2207/20* (2013.01); *A01K 2207/30* (2013.01); *A01K 2227/105* (2013.01); *A01K 2267/03* (2013.01); *C12Q 2600/158* (2013.01); *G01N 2333/705* (2013.01); *G01N 2333/78* (2013.01); *G01N 2800/368* (2013.01); *G09B 23/30* (2013.01)

(58) Field of Classification Search
CPC .... G01N 33/689; A61B 5/4343; A61B 17/42; A01K 2227/105; A01K 67/027; A01K 2207/30; A01K 2207/20; G09B 23/30
See application file for complete search history.

(56) References Cited

U.S. PATENT DOCUMENTS

2012/0270747 A1   10/2012   Elovitz

FOREIGN PATENT DOCUMENTS

JP   2008-125452   6/2008

OTHER PUBLICATIONS

Castanon et al. Risk of preterm delivery with increasing depth of excision for cervical intraepithelial neoplasia in England: nested case-control study BMJ 2014; 349: g6223 (Year: 2014).*
MyHealth.Alberta.ca. "Loop Electrosurgical Excision Procedure (LEEP): What to Expect at Home" Updated Feb. 2015, Archived Oct. 2015 https://web.archive.org/web/20151001023133/https://myhealth.alberta.ca/Health/aftercareinformation/pages/conditions.aspx?hwid=av2657 (Year: 2015).*
Elovitz et al., "Animal models of preterm birth", Trends in Endocrinology and Metabolism, vol. 15, No. 10, Dec. 2004, pp. 479-487.
Akgul et al., "Dynamic Changes in Cervical Glycosaminoglycan Composition during Normal Pregnancy and Preterm Birth", Endocrinology, 153(7), Jul. 2012, pp. 3493-3503.
Rinaldi et al., "Ultrasound-Guided Intrauterine Injection of Lipopolysaccharide as Novel Model of Preterm Birth in the Mouse", The American Journal of Pathology, vol. 185, No. 5, May 2015, pp. 1201-1206.
Chosun Media—Health Chosun, In case of a cervical cancer, the risk of premature birth is still high even though it has been cured at an early stage (intraepithelial cancer stage), May 16, 2012, 4 pages.
Torres et al., "A Rat Embryo Staging Scale for the Generation of Donor Tissue for Neural Transplantation", Cell Transplantation, Aug. 22, 2007, vol. 17, pp. 535-542.
Castanon et al., "Risk of preterm delivery with increasing depth of excision for cervical intraepithelial neoplasia in England: nested case-control study", BMJ, Nov. 5, 2014, vol. 349, pp. 1-11.
Yoon et al., "A Rabbit Model for Bacteria-induced Preterm Delivery by Hysteroscopy-guided Intracervical *E. coli* Inoculation and Its Relevance to Intraamniotic Infection", Department of Obstetrics and Gynecology, College of Medicine, Seoul National University, Seoul, Korea, vol. 38, No. 10, Oct. 1995, pp. 1819-1828.

* cited by examiner

*Primary Examiner* — Shin Lin Chen
(74) *Attorney, Agent, or Firm* — Duane Morris LLP; Gregory M. Lefkowitz; Brandon A. Chan

(57) ABSTRACT

The present invention relates to a method for producing an animal model of preterm birth and an animal model of preterm birth produced by the method. The animal model of the present invention can be effectively applied to investigate the causes and symptoms of preterm birth induced by cervical injury. The mortality rate of the animal model according to the present invention is low until preterm birth despite its induced preterm birth. In addition, the animal model of the present invention is produced in a higher yield than any other existing model. Furthermore, the preterm birth of the animal model according to the present invention is induced at a desired time point. Due to these advantages, the animal model of the present invention can be effectively applied to investigate the causes and mechanisms of preterm birth. The mortality rate of premature neonates born from the animal model of the present invention is considerably low and the premature neonates are immature. Therefore, the animal model of the present invention can be effectively applied to studies on complications of premature neonates.

13 Claims, 10 Drawing Sheets

[Fig. 1a]
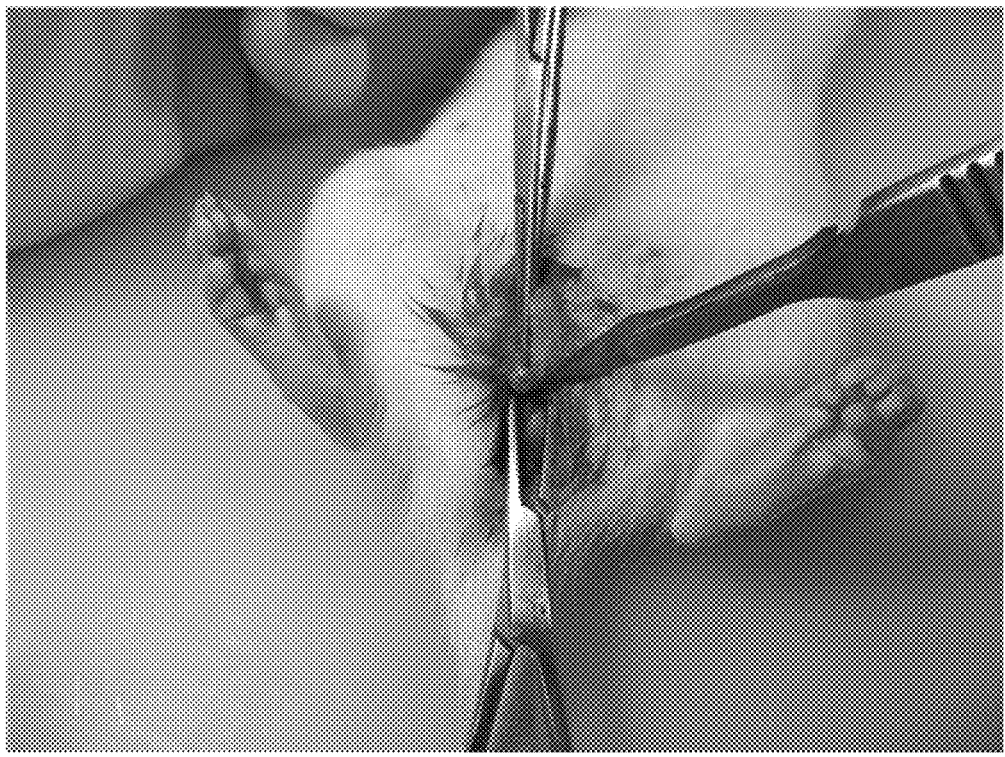
[Fig. 1b]

[Fig. 2]
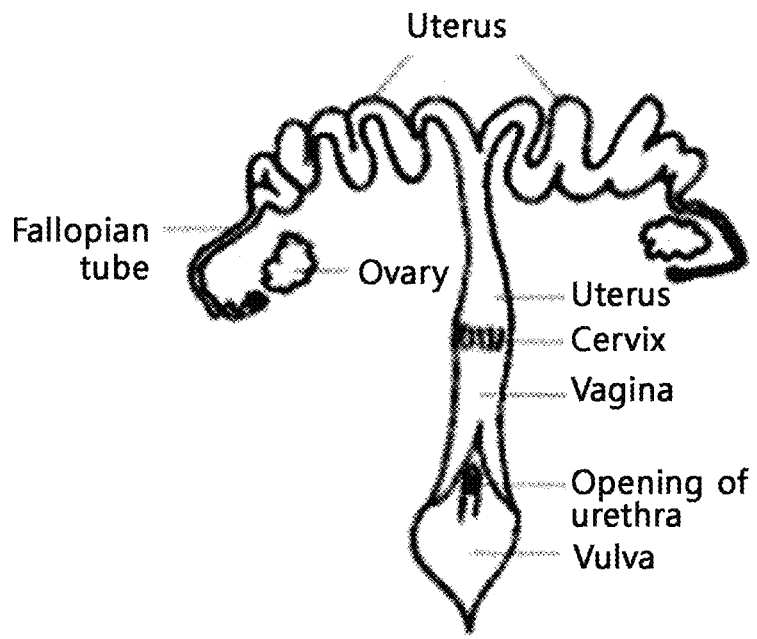
[Fig. 3]
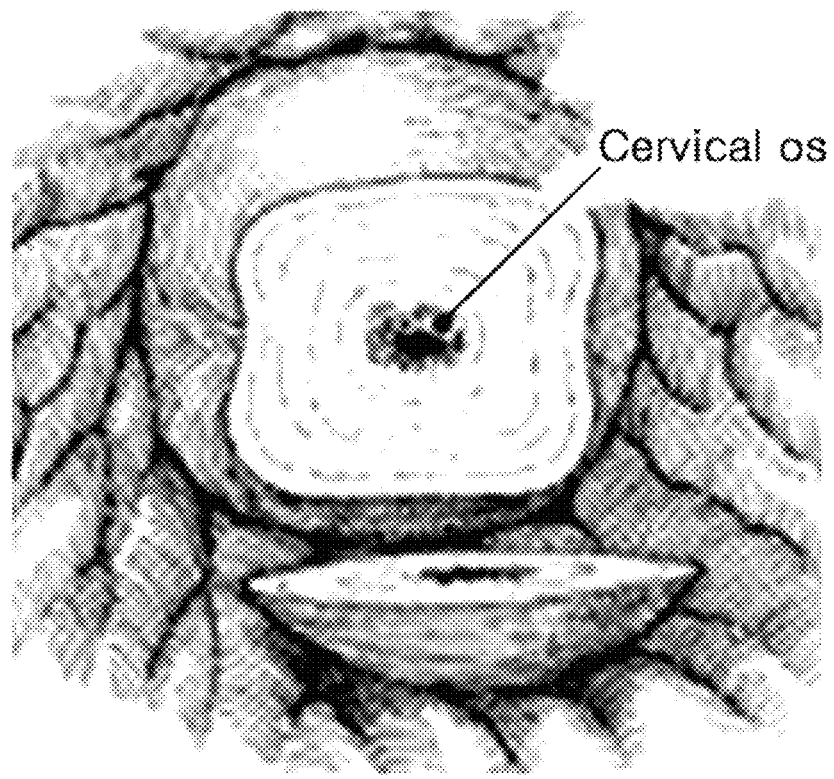

[Fig. 4a]
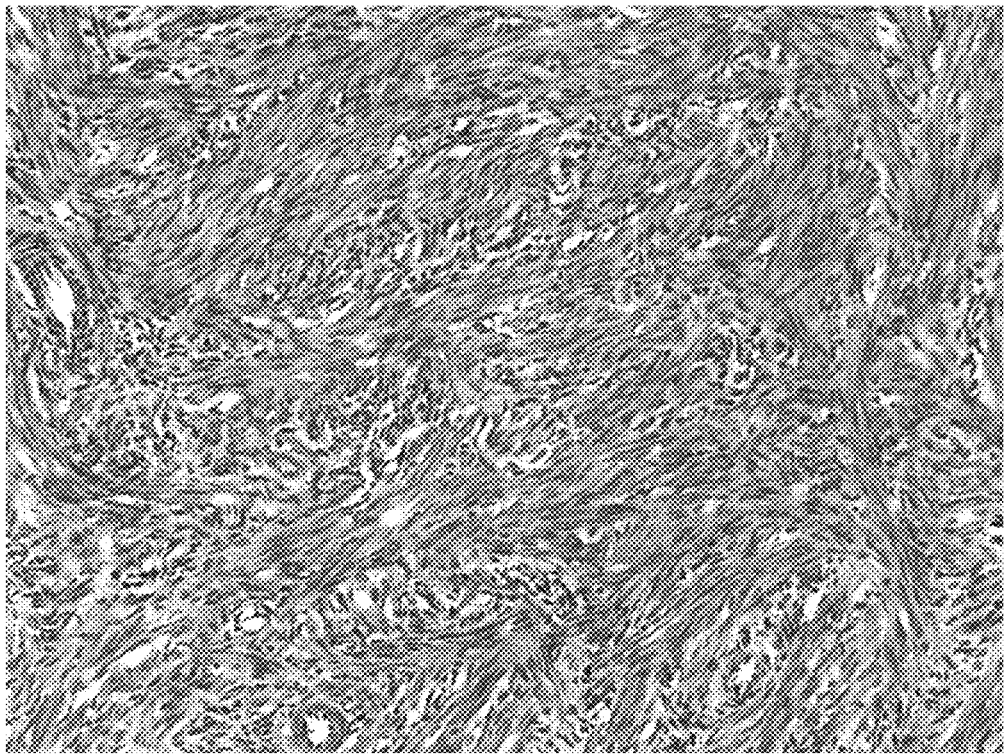
[Fig. 4b]
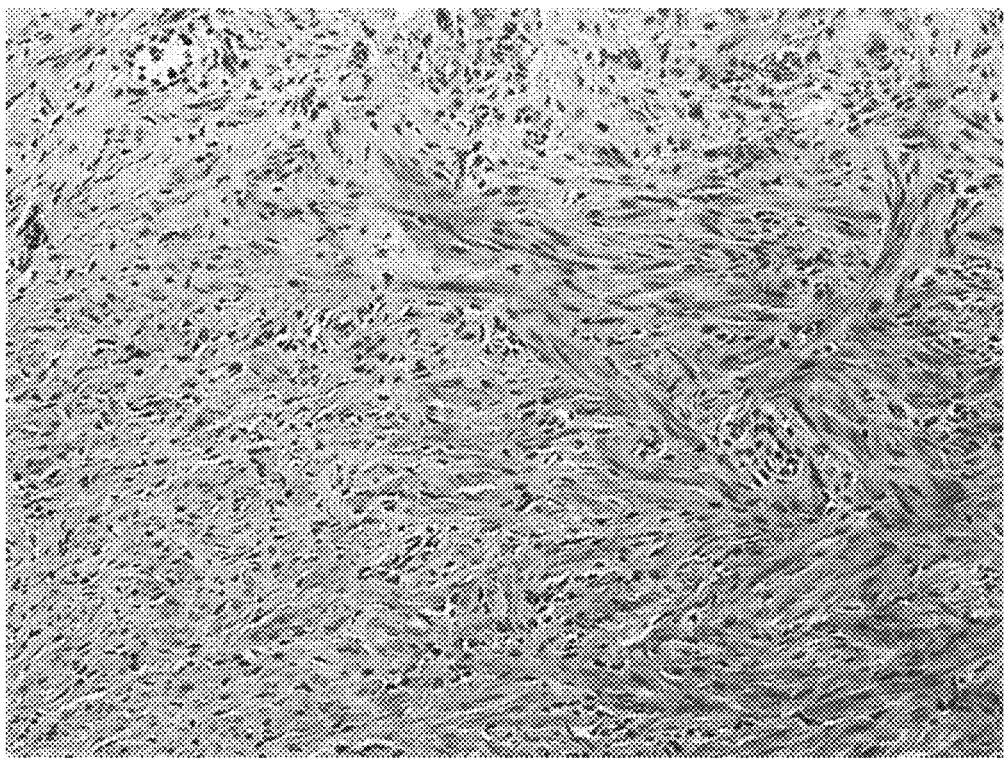

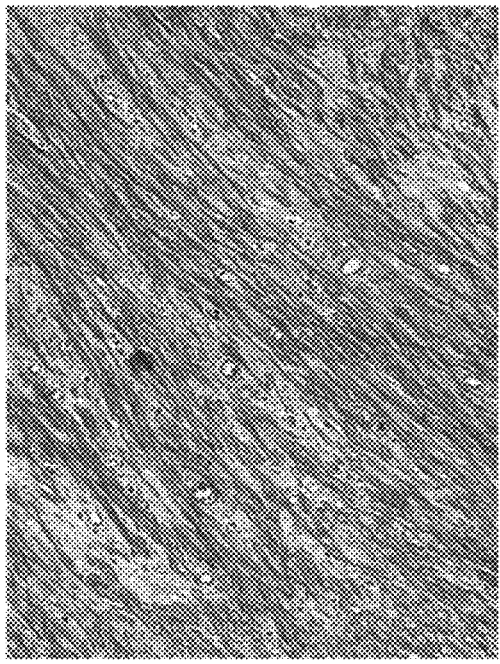
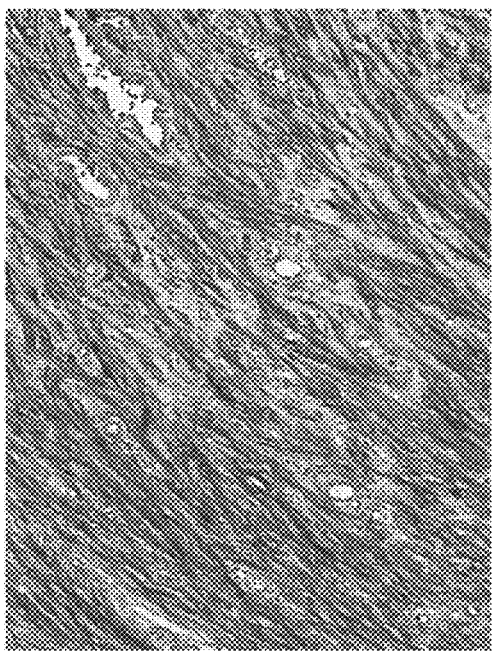
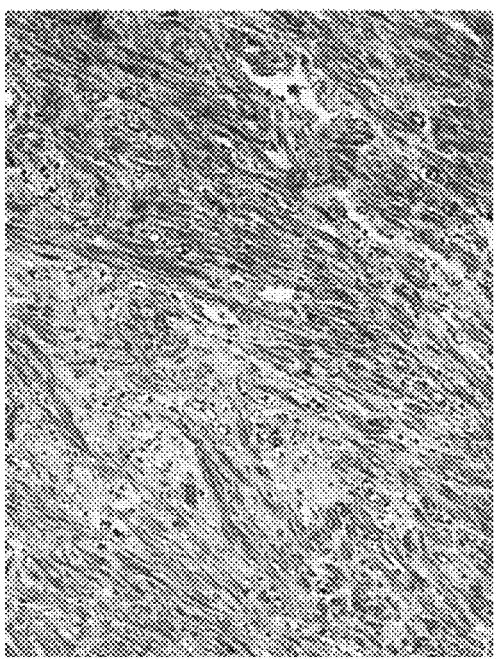
FIG. 6a

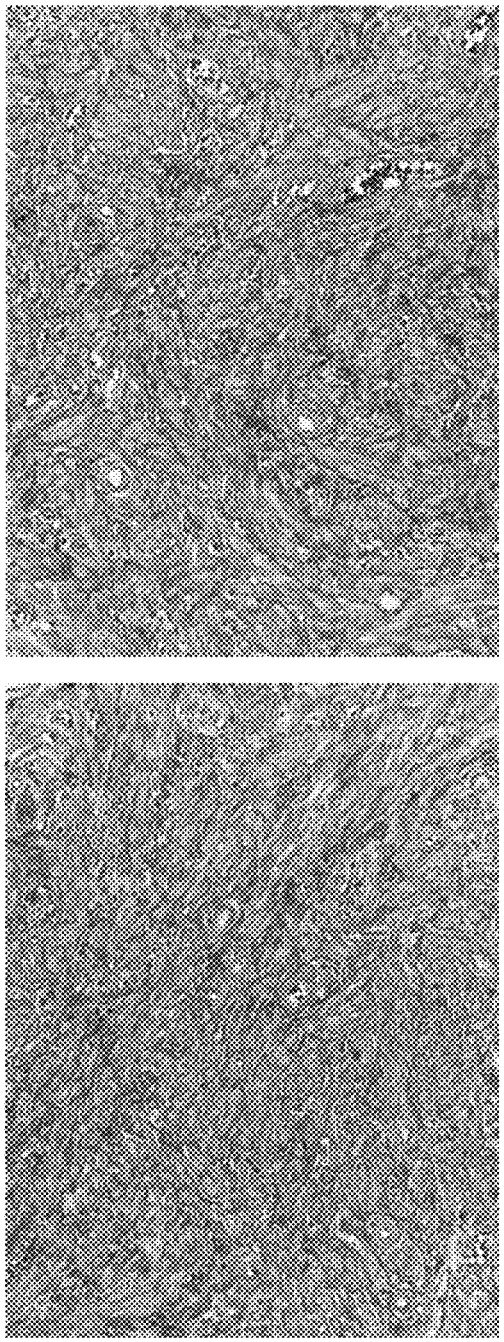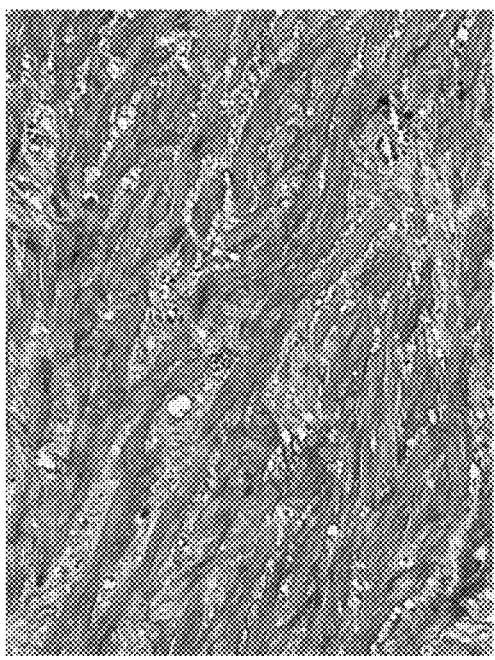
FIG. 6b

[Fig. 7a]
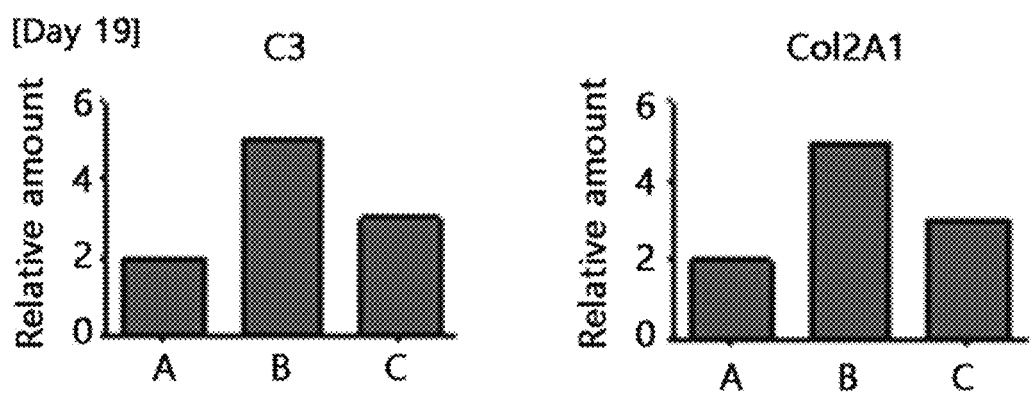
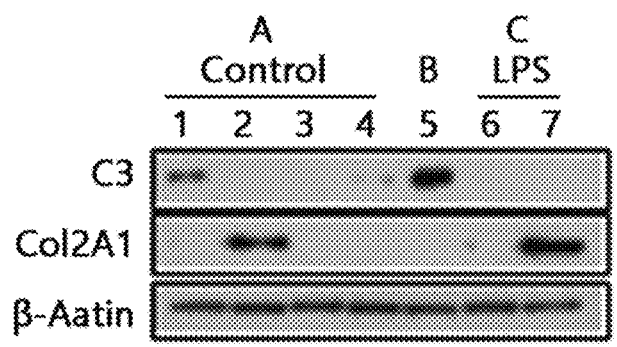

[Fig. 7b]
[Immediately after parturition]
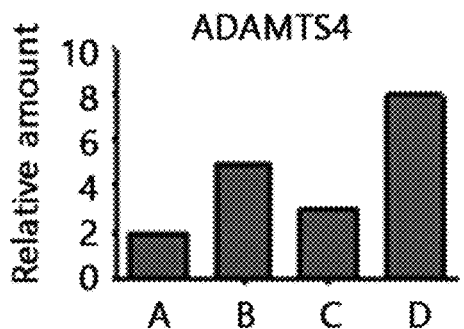
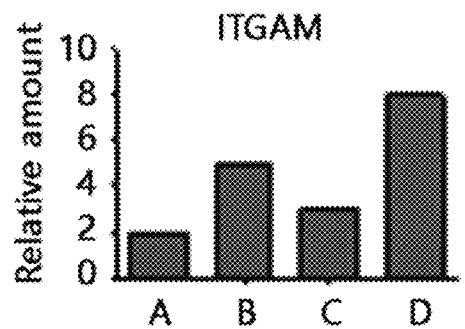
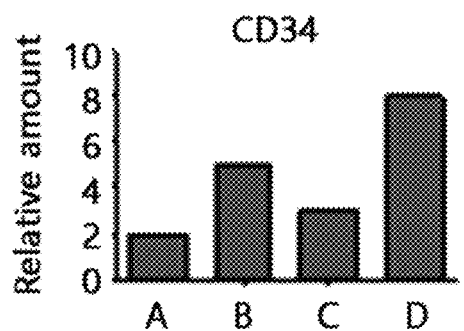
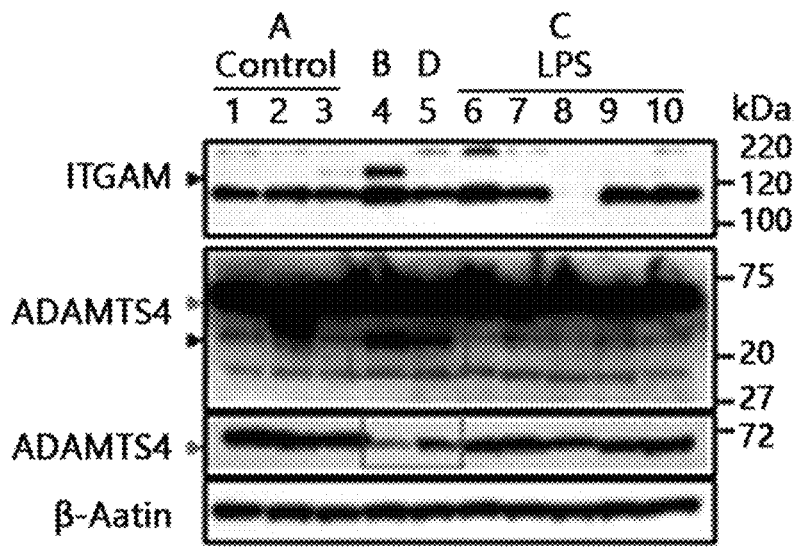
- ITGAM : ~160kDa
- ADAMTS4 : 100~75kDa
- No expression was observed for CD34

[Fig. 8]
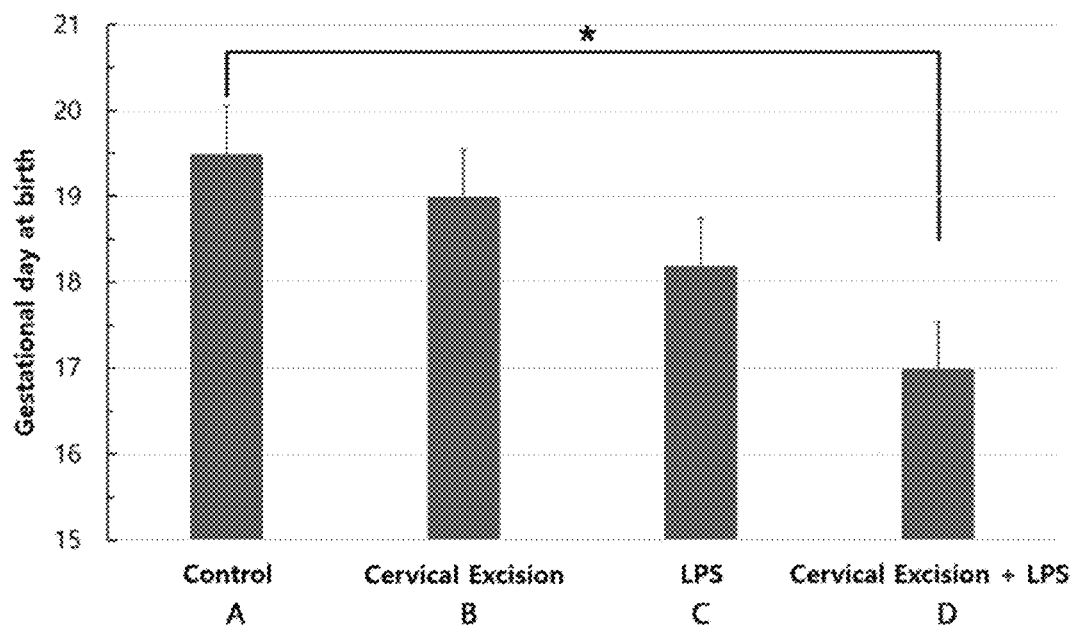

METHOD FOR PRODUCING ANIMAL MODEL OF PRETERM BIRTH AND ANIMAL MODEL OF PRETERM BIRTH PRODUCED BY THE METHOD

CROSS-REFERENCE TO RELATED APPLICATIONS

This application is a § 371 national stage entry of International Application No. PCT/KR2017/004148, filed on Apr. 18, 2017, which claims priority to South Korean Patent Application No. 10-2016-0055878, filed on May 6, 2016, and South Korean Patent Application No. 10-2017-0047866, filed on Apr. 13, 2017, the entire contents of which are incorporated herein by reference.

TECHNICAL FIELD

The present invention relates to a method for producing an animal model of preterm birth and an animal model of preterm birth produced by the method.

BACKGROUND ART

Preterm birth refers to the birth of a baby between 20 weeks and 37 weeks of pregnancy. Preterm birth accounts for approximately 12% of all pregnancies and is the most common cause of neonatal morbidity and mortality around the world. According to a US report, the socioeconomic cost of preterm birth was estimated to be $2.6 trillion in 2005.

Preterm birth is caused by various factors. Infection is currently known as the most important mechanism of preterm birth but such an inflammatory response is not always involved in the mechanism of inducing preterm birth. This fact makes it difficult to develop clear preventive and therapeutic approaches for preterm birth. Whatever its causes, preterm birth involves cervical maturation and dilatation. The clinical probability of preterm birth increases markedly in women who have undergone cervical conization or miscarriage and as a result whose cervix has been removed or injured.

As such, the role of the cervix in association with preterm birth is very important. Since damage to the cervical structure or tissue increases the risk of preterm birth, there is a need for a trial to thoroughly elucidate the relationship between preterm birth and the cervix to lower the probability of preterm birth. Despite this trial, studies remain in the early stages.

The cervix is anatomically located at the entrance of the uterus and is connected to the vagina. The cervix is a rigid structure that remains closed before changes associated with parturition occur. The cervix is a fibrous, connective tissue consisting of an extracellular matrix composed of type I and II collagens, elastin, and proteoglycans, smooth muscles, and blood vessels. There is a need to scrutinize the structure or tissue of the cervix and elucidate the relationship between the cervix and preterm birth in order to provide animal models for the purpose of further lowering the probability of preterm birth.

On the other hand, rodent models of preterm birth are known whose preterm birth is induced by injecting lipopolysaccharide between two gestational sacs near the cervix at day 15-17 of gestation. However, these animal models cannot be effectively utilized because the injection of lipopolysaccharide leads to a decrease in preterm birth yield and an excessive increase in mortality.

In this connection, experimental rabbit models whose preterm birth is induced by intrauterine infection after injection of bacteria into the uteri of pregnant rabbits through a hysteroscope are disclosed in Obstetrics & Gynecology Science, Vol. 38, No. 10 (1995), pp. 1819-1828 ("Non-Patent Document 1")). However, the experimental procedure is complicated, the animal models are expensive to purchase and require high management costs, and it takes a very long time for symptoms to be reproduced. For these reasons, studies on the mechanism of preterm birth and the development of therapies for preterm birth using the animal models are limited.

DETAILED DESCRIPTION OF THE INVENTION

Problems to be Solved by the Invention

The present invention has been made in an effort to solve the above-described problems, and it is an object of the present invention to provide a method for producing an animal model of preterm birth that appropriately reflects a situation in which preterm birth is induced by damage to the cervix.

Means for Solving the Problems

A method for producing an animal model of preterm birth according to one feature of the present invention includes 1) excising the cervix of a mammal through the vagina of the mammal, 2) allowing the mammal to recover, 3) making the mammal pregnant, and 4) injecting lipopolysaccharide (LPS) intrauterinely or intraperitoneally into the mammal.

An animal model of preterm birth according to another feature of the present invention is produced by the method.

Effects of the Invention

The method of the present invention appropriately reflects a situation in which preterm birth is induced by damage to the cervix and is effective in providing an animal model of preterm birth based on this situation. In addition, the animal model of the present invention can be used to control and predict the time when preterm birth occurs. The animal model of the present invention can provide premature neonates.

The animal model of the present invention can reproduce a situation close to actual preterm birth induced by injury, damage or loss of the cervix compared to existing models. The animal model of the present invention can reproduce symptoms similar to those of actual patients, thus being suitable for use as a preclinical experimental model. Therefore, the animal model of the present invention is expected to greatly contribute to studies on preterm birth.

In addition, the animal model of the present invention can be effectively applied to the development of biomaterials for the investigation of the mechanism of preterm birth and therapies for preterm birth. The mortality rate of premature neonates born from the animal model of the present invention is low and the premature neonates are immature. Therefore, the animal model of the present invention can be effectively applied to studies on complications of premature neonates.

BRIEF DESCRIPTION OF THE DRAWINGS

FIG. 1 shows photographic images of cervical excision performed in Example 1.

FIG. 2 shows the anatomical locations of the uterus and cervix of a rodent.

FIG. 3 is a model showing cervical injury and loss.

FIG. 4 shows images showing (a) proximal and (b) distal portions of the cervix removed from an animal in group D by cervical excision in Example 1 after staining with Masson's trichrome, which were taken in Experimental Example 2.

FIG. 6 shows images of the cervices removed from animals in groups by cervical excision in Example 1 after staining with Masson's trichrome, which were taken in Experimental Example 6.

FIG. 7 shows RNA and protein expressions measured in Experimental Example 7.

FIG. 8 shows the waiting periods of animals in groups A, B, C, and D injected intrauterinely with lipopolysaccharide until parturition, which were measured in Experimental Example 8.

BEST MODE FOR CARRYING OUT THE INVENTION

Figure 5A:
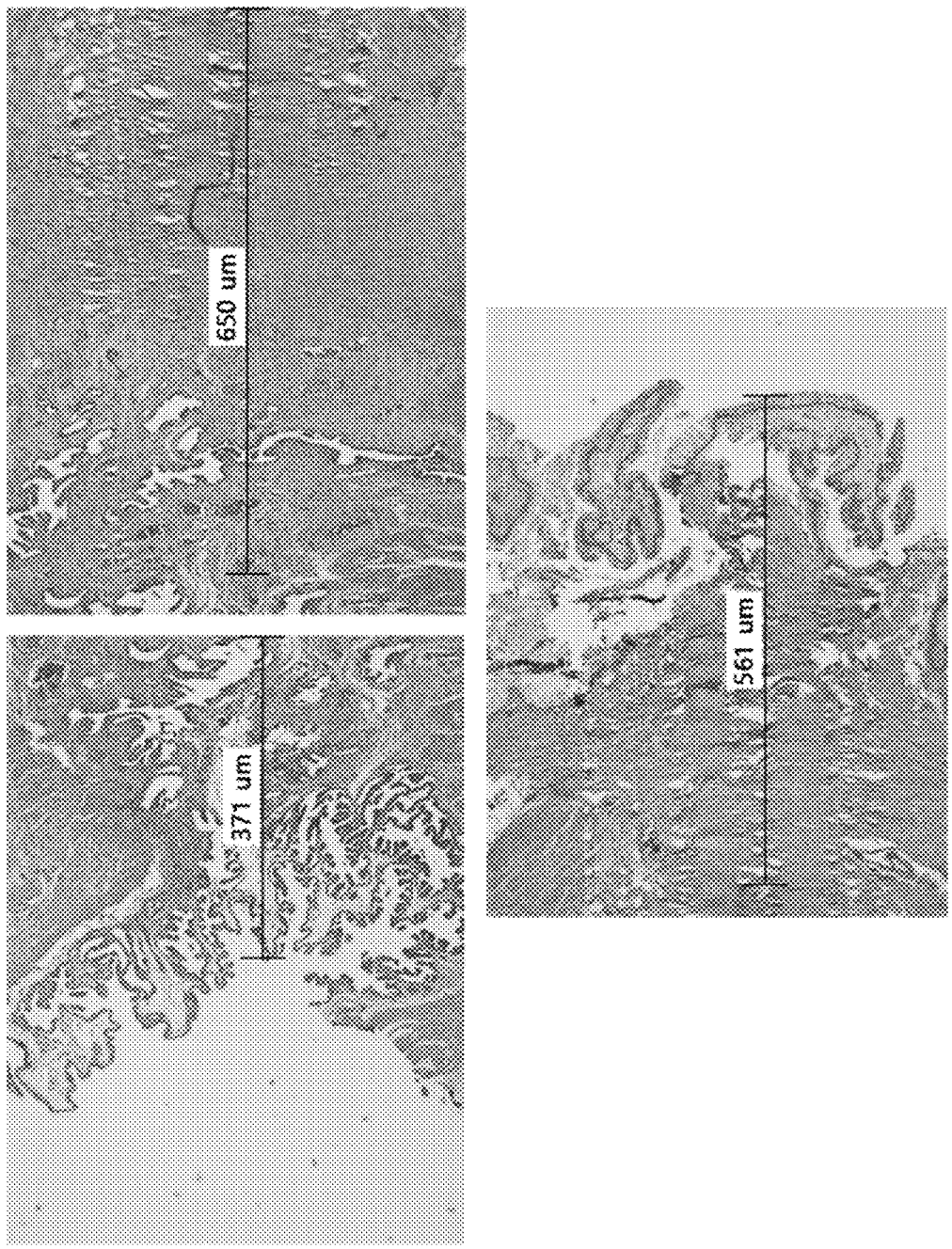
FIG. 5 shows images showing the lengths of the cervices of (a) animals in a group having received surgery performed in Example 1 and (b) animals in a group having received no surgery performed in Example 1, which were measured in Experimental Example 6.

Thus, the present inventor has earnestly and intensively conducted research to develop an animal model whose preterm birth is induced at an accurate time point while maintaining a very low mortality rate until preterm birth, and as a result, has succeeded in developing an improved method for producing an animal model of preterm birth. The present invention has been accomplished based on this finding.

Specifically, a method for producing an animal model of preterm birth according to the present invention includes 1) excising the cervix of a mammal through the vagina of the mammal, 2) allowing the mammal to recover, 3) making the mammal pregnant, and 4) injecting lipopolysaccharide (LPS) intrauterinely or intraperitoneally into the mammal.

In step 1), the cervix of a mammal is excised through the vagina of the mammal. Preferably, the cervix is excised without cutting the abdomen open. For example, the cervix may be excised through direct access to the vagina. The cervix may be excised with a suitable tool such as a scalpel. Preferably, the entrance of the vagina is opened for access to the vagina. For this opening, the vaginal wall is firmly held with forceps. The opening of the entrance of the vagina is to secure a sufficient field of view, allowing direct excision of the cervix. In contrast, cervical excision by laparotomy may lead to a high mortality rate and may require a long recovery time. Therefore, the direct cervical excision in step 1) does not lead to a high mortality rate and shortens the time needed for recovery. As a result of the direct cervical excision, resistance to an increasing intrauterine pressure is reduced, resulting in a high probability of preterm birth.

In step 1), it is preferred that 30 to 100% of the cervix is excised. More preferably, 60 to 100% of the cervix is excised. If less than 30% of the cervix is excised, the probability of preterm birth is not sufficiently high. If less than 60% of the cervix is excised, the probability of preterm birth varies depending on the mammalian species.

In step 2), the mammal is preferably recovered for 5 to 30 days, more preferably from 15 to 20 days, most preferably 20 to 25 days. A recovery period of less than 5 days is too short to recover from the injury, leading to a low probability of pregnancy. A recovery period of less than 15 days decreases the pregnancy rate to 60%. A recovery period exceeding 25 days, a maximum of 30 days, is undesirable in terms of efficiency because it takes a long time to produce the desired animal model.

In step 4), lipopolysaccharide (LPS) is injected intrauterinely or intraperitoneally into the mammal.

The intrauterine or intraperitoneal injection of lipopolysaccharide (LPS) after the cervical excision and gestation enables the induction of preterm birth at a predictable time point. According to the prior art, an excess amount of lipopolysaccharide is injected without cervical excision. In this case, the likelihood of stillbirth is increased by a factor of at least two due to inflammatory responses induced by lipopolysaccharide. The administration of lipopolysaccharide was found to affect other symptoms as well as preterm birth. In contrast, according to the method of the present invention, the intrauterine or intraperitoneal injection of an appropriate amount of lipopolysaccharide (LPS) at an appropriate time point during gestation after the cervical injection is effective in greatly increasing the success rate of preterm birth while considerably lowering the probability of maternal mortality and stillbirth. In addition, the method of the present invention is advantageous in that the time when preterm birth occurs can be controlled and predicted, specifically because preterm birth occurs within a predetermined time after the injection of lipopolysaccharide.

The lipopolysaccharide is preferably injected into the uterine cavity, most preferably between the first and second gestational sacs in the distal portion of the uterus, which is effective in achieving preterm birth. Lipopolysaccharide is a representative material that stimulates inflammatory cascade responses. Injection of LPS via routes other than into the uterine cavity may cause systemic infection although the amount of the lipopolysaccharide injected is in the range defined below.

The lipopolysaccharide is injected in an amount of 20 to 500 µg, preferably 50 to 150 µg, per animal. If the amount of the lipopolysaccharide is less than the lower limit, it is difficult to induce preterm birth. Meanwhile, if the amount of the lipopolysaccharide exceeds the upper limit, symptoms (inflammatory responses) other than preterm birth are caused, resulting in a high probability of stillbirth or maternal mortality. The amount of the lipopolysaccharide injected can be appropriately determined depending on the weight of the animal. That is, it is preferred that the amount of the lipopolysaccharide increases with increasing weight of the animal.

The lipopolysaccharide is preferably injected when 65 to 80% of the total gestation period passes. If the lipopolysaccharide is injected at a time point less than 65% of the gestation period, the probability of stillbirth increases. Meanwhile, if the lipopolysaccharide is injected at a time point more than 80% of the gestation period, the probability of inducing preterm birth decreases considerably. For example, the lipopolysaccharide is injected at day 16 of gestation when the gestation period is from 20 to 23 days.

Injection of the lipopolysaccharide under the conditions defined above can induce parturition within 10 to 96 hours, preferably 12 to 48 hours. That is, the time when preterm birth occurs can also be controlled and predicted from the time point when the lipopolysaccharide is injected.

The mammal is a non-human mammal but is not particularly limited thereto. The mammal is preferably a rodent. More preferably, the mammal is selected from the group consisting of rats, mice, squirrels, hamsters, guinea pigs, beavers, moles, rabbits, dogs, pigs, cows, sheep, and primates.

MODE FOR CARRYING OUT THE INVENTION

The present invention will be explained in detail in such a manner that those with ordinary knowledge in the art can easily carry out the invention with reference to the following examples. The invention may, however, be embodied in many different forms and should not be construed as limited to the exemplary embodiments set forth herein.

Example 1

In this example, female Sprague-Dawley rats, aged 5-10 weeks, were used. After the cervix of each animal was excised with a scalpel through the vagina under anesthesia. The vaginal wall was firmly held with forceps and the entrance of the vagina was opened to secure a sufficient field of view. Thereafter, the protruding cervix was excised with a knife as needed. This cervical excision is shown in FIG. 1a. FIG. 2 shows the anatomical locations of the uterus and the cervix of a rodent. FIG. 3 is a model showing cervical injury and loss.

Example 2

3 weeks after cervical excision, a female rat was allowed to copulate with a male rat. At day 16 of gestation, 100 μg of lipopolysaccharide (LPS)/100 μL of NS was injected between the first and second gestational sacs in the distal portion of the right uterine horn of the pregnant rodent. The day when a mucus plug was found at the entrance of the vagina was regarded as day 1 of gestation. FIG. 1b is a photograph showing injection of lipopolysaccharide.

Comparative Example 1

Cervical excision was performed by laparotomy, unlike in Example 1. Specifically, 25 mg/kg of ketamine and 10 mg/kg of xylazine were administered intraperitoneally for anesthesia. The abdominal wall was opened by a median incision of the lower abdomen to expose the uterus. The uterus was lifted up and the posterior vaginal wall was incised to expose the cervix. The protruding cervix was excised, and then the vaginal wall was closed with 4-0 polyglactin 910 (Vicryl; Ethicon, Seoul, Korea) sutures. The muscle, fascia, and skin were closed with 3-0 polyglactin 910 (Vicryl) sutures.

Comparative Example 2

Lipopolysaccharide was injected between the first and second gestational sacs in the distal portion of the uterus without any surgical procedure, unlike in Example 2.

Specifically, a female rat was allowed to copulate with a male rat. At day 16 of gestation, 50 μg of lipopolysaccharide (LPS)/100 μL of NS was injected between the first and second gestational sacs in the distal portion of the right uterine horn of the pregnant rodent.

Experimental Example 1: Evaluation of the Surgical Procedures for Producing Animal Models of Preterm Birth Whose Cervices were Injured For this experiment, rats were divided into two groups. The cervices of the rats in one group were excised by the procedure of Example 1 and those in the other group were excised by the procedure of Comparative Example 1. Anatomical recovery and complications of the cervices of the rats in the two groups were investigated after recovery for a predetermined period.

Experimental Animals

This study was approved by the Ethics Committee for Animal Studies at Korea University (KUIACUC-2014-161). Forty-five 10-week-old female Sprague-Dawley rats were randomly divided into 9 groups, 5 animals per group. The abdomens of the animals in group A as a control group were cut open and their abdominal walls were reclosed without any surgical operation. The vaginas of the animals in group B were incised to expose the cervices, the exposed cervices were excised, the vaginas were reclosed, and the abdominal walls were closed (Comparative Example 1). The cervices of the animals in group C were removed through the vaginas (Example 1). At day 3, day 7, and day 14, the uteri of the animals in groups A, B, and C were removed and weighed. The uteri were fixed in formalin for histological examination.

Cervical Excision

Before the cervical excision of Example 1 and Comparative Example 1, 25 mg/kg of ketamine and 10 mg/kg of xylazine were administered intraperitoneally to the animals for anesthesia in accordance with a previous method.

Mortality Rate

To evaluate postsurgical stability, the mortality rates of the animals were calculated by recording whether the animals were dead or alive.

Statistical Analysis

Data were expressed as mean±standard deviation or standard error. Statistical comparisons between all groups were done using one-way analysis of variance (ANOVA) and the differences were calculated using the Tukey's test. A value of $P<0.05$ was considered statistically significant.

Results

The experimental results are shown in Table 1. As can be seen from the results in Table 1, no substantial differences in body weight between groups A, B, and C at the day of surgery were found but the body weights of the animals in group B having undergone laparotomy were significantly small compared to those of the animals in the other groups at day 3 of recovery. However, these differences in body weight gradually decreased with increasing recovery period (at day 7 and day 14). After day 14 of recovery, there was no substantial difference in body weight between the animals in group B having undergone laparotomy and the animals in group C without laparotomy.

The time of the surgical procedure of Example 1 is less than one-third of that of the laparotomy of Comparative Example 1. The mortality rate after the surgery of Example 1 was one-half of that after the laparotomy of Comparative Example 1. Therefore, the procedure of Example 1 is believed to be advantageous for model production over the laparotomy of Comparative Example 1.

TABLE 1

|  | A-3 (n = 5) | B-3 (n = 5) | C-3 (n = 5) | A-7 (n = 5) | B-7 (n = 5) | C-7 (n = 5) | A-14 (n = 5) | B-14 (n = 5) | C-14 (n = 5) | P |
|---|---|---|---|---|---|---|---|---|---|---|
| Weight (g), at week 0 | 199 ± 3.9 | 196.9 ± 8.1 | 194.5 ± 5.5 | 204.7 ± 5.4 | 197.6 ± 7.8 | 195.6 ± 4.3 | 204.9* ± 8.9 | 197.9 ± 9.7 | 199.5 ± 4.8 | 0.227 |
| Examination time (min) | 202.9 ± 5.8 | 193.6 ± 10.6 | 207.0 ± 3.5 | 218.6 ± 9.6 | 211.6 ± 4.5 | 225.0 ± 4.8 | 237.4 ± 17.1 | 245.5 ± 15.7 | 232.6 ± 7.8 | <0.001 |
| Surgical time (min) |  | 26.0 ± 1.6 | 8.0 ± 0.7 |  | 27.2 ± 1.9 | 8.2 ± 0.8 |  | 26.2 ± 1.3 | 8.0 ± 0.7 | <0.001 |
| Mortality rate (%) | 0 | 40.0 | 20.0 | 0 | 20.0 | 0 | 0 | 20.0 | 20.0 | 0.141 |

Experimental Example 2: Evaluation of Extents of Cervical Loss and Injury in Example 1

The cervical excision performed in Example 1 is a safe and efficient surgery compared to the laparotomy performed in Comparative Example 1. Thus, the present inventor decided to perform the cervical excision of Example 1 in subsequent experiments. After anesthesia, 10-week-old female Sprague-Dawley rats were grouped depending on the extent of cervical excision. Different portions (⅓, ½, and ⅔) of the cervices were excised. Anatomical recovery and complications of the cervices in the animals in the two groups after recovery for a predetermined period were investigated.

Experimental Animals

This study was approved by the Ethics Committee for Animal Studies at Korea University (KUIACUC-2014-161). Forty 10-week-old female Sprague-Dawley rats were randomly divided into 8 groups, 5 animals per group. The animals in group A as a control group underwent no anesthesia and no cervical excision. A portion (⅓) of the cervix of each animal in group B was removed by vaginal operation. A portion (½) of the cervix of each animal in group C was removed by vaginal operation. A portion (⅔) of the cervix of each animal in group D was removed by vaginal operation. At day 7 and day 14, the uteri of the animals in groups A, B, C, and D were removed and weighed. The uteri were fixed in formalin for histological examination.

Cervical Excision (Vaginal Operation)

The cervical excision of Example 1 was performed after intraperitoneal administration of 25 mg/kg of ketamine and 10 mg/kg of xylazine for anesthesia in accordance with a previous method. The protruding cervices were excised through the vaginas (see FIG. 1a).

Histochemical Staining with Masson's Trichrome for Muscle-Collagen Ratio Measurement Three sections per sample were used for quantitative analysis after staining with Masson's trichrome, as shown in FIGS. 4a and 4b. Three regions per section were randomly selected, the areas (smm) of the stained muscle and collagen sites were measured using a microscope at a magnification of 200×, and the muscle-collagen ratios were calculated. The sample shown in FIG. 4 was the cervix excised from one of the animals in group D having undergone the cervical excision of Example 1.

Results

The experimental results are summarized in Table 2. In Table 2, each group is designated as "corresponding group-recovery period (day)". For example, "C-14" indicates the animals in group C whose cervices were partially (½) excised and who were allowed to recover for 14 days. There were no substantial differences in muscle-collagen ratio in the distal portions of the cervices between the groups.

TABLE 2

|  | A-7 (n = 5) | B-7 (n = 5) | C-7 (n = 5) | D-7 (n = 5) | A-14 (n = 5) | B-14 (n = 5) | C-14 (n = 5) | D-14 (n = 5) | P |
|---|---|---|---|---|---|---|---|---|---|
| Weight (g), at week 0 | 212 ± 5.8 | 215.6 ± 5.6 | 190.5 ± 39.1 | 212.3 ± 6.7 | 206.6 ± 4.9 | 216.9 ± 5.0 | 216.8 ± 5.4 | 214.9 ± 7.8 | 0.133 |
| Muscle-collagen ratio (%) | 98.8 ± 5.5 | 98.2 ± 73.9 | 85.7 ± 51.9 | 52.5 ± 19.9 | 66.3 ± 49.1 | 103.5 ± 46.1 | 106.8 ± 97.3 | 33.4 ± 4.7 | 0.529 |

Experimental Example 3: Evaluation of Recovery Periods Before Copulation with Males after Cervical Loss and Injury in Example 1

10-week-old female Sprague-Dawley rats were grouped depending on the recovery period (7, 14, and 28 days) after cervical excision. After the animals were allowed to copulate with males, their pregnancy rates were recorded. The pregnancy rate of 10-week-old female Sprague-Dawley rats is generally ~79-81%.

Experiment Animals

This study was approved by the Ethics Committee for Animal Studies at Korea University (KUIACUC-2014-161). Twenty-seven 10-week-old female Sprague-Dawley rats were randomly divided into 9 groups, 3 animals per group. The animals in group A as a control group underwent no anesthesia and no surgery. A portion (⅓) of the cervix of each animal in group B was removed by vaginal operation. The cervix of each animal in group C was completely excised by vaginal operation. 7, 14, and 28 days after the surgery, the animals were allowed to copulate with males and wait until pregnancy has been confirmed.

Variables Associated with Parturition and Neonates

Gestation was determined by observing changes in body weight, behavioral, and abdominal changes. Pregnant animals were individually managed and gestation periods were calculated from the surgery day until parturition. The number, body weight, and length of the neonates were measured.

Results

The experimental results are summarized in Table 3. Groups A, B, and C all showed high pregnancy rates. The values of groups B and C were lower than those of group A but the differences were not statistically significant. Therefore, these models were confirmed to be suitable for gestation, which is a prerequisite for preterm birth. In Table 3, each group is designated as "corresponding group-recovery period (week)". For example, "B-2" indicates the animals in group B whose cervices were partially (½) excised and who were allowed to recover for 2 weeks.

The periods starting from cervical excision until parturition instead of starting from the time of copulation with males after recovery from cervical excision were calculated. As a result, the period from cervical excision until parturition, of course, increased with increasing recovery period (1, 2, and 4 weeks) (P=0.002). Considering that the gestation period of rats is approximately 20 to 22 days, most of the animals in the groups copulated with males and became pregnant after ~3 weeks following cervical excision.

There were no statistically significant differences in the number of neonates irrespective of the recovery period after cervical excision. Of course, the body weight and height of neonates increased with increasing recovery period (body weight P=0.026, height P=0.037)

manner as in Example 2. 21 days after surgery, the animals were allowed to copulate with males and wait until pregnancy has been confirmed. In this experiment, pregnancy rates depending on the recovery period after cervical excision were investigated. As a result, the pregnancy rate decreased considerably when the recovery period was as short as 1-2 weeks and no substantial difference in pregnancy rate was found when the recovery period was ≥3 weeks. Thus, a minimum of 21 days was allowed for recovery.

Cervical Excision

Cervical excision was performed as shown in FIG. 1 and isoflurane was used for inhalation anesthesia.

Gestation Period Measurement

The day when a plug was found at the entrance of the vagina after copulation was regarded as day 1 of gestation and the waiting period until parturition was calculated.

Statistical Analysis

Data were expressed as mean±standard deviation or standard error. Statistical comparisons between all groups were

TABLE 3

|  | A-1 (n = 3) | B-1 (n = 3) | C-1 (n = 3) | A-2 (n = 3) | B-2 (n = 3) | C-2 (n = 3) | A-4 (n = 3) | B-4 (n = 3) | C-4 (n = 3) | P |
|---|---|---|---|---|---|---|---|---|---|---|
| Weight at the time of examination (g) | 222.4 ± 8.3 | 222.3 ± 6.7 | 227.9 ± 5.2 | 223.7 ± 1.5 | 225.2 ± 3.6 | 226.0 ± 7.4 | 225.2 ± 3.6 | 223.9 ± 8.3 | 225.3 ± 6.2 | 0.972 |
| Period from surgery until parturition (day) | 41.0 ± 8.7 | 46.0 ± 15.5 | 38.0 ± 7.9 | 60.7 ± 11.0 | 56.0 ± 1.4 | 74.0 ± 2.8 | 69.7 ± 2.5 | 65.7 ± 0.6 | 67.0 | 0.002 |
| Pregnancy probability (%) | 100 | 100 | 100 | 100 | 66.7 | 100 | 100 | 100 | 50 |  |
| Number of neonates | 14.7 ± 2.1 | 14.0 ± 1.0 | 15.3 ± 1.2 | 14.3 ± 0.6 | 10.0 ± 5.7 | 10.0 ± 5.7 | 13.0 ± 2.0 | 12.3 ± 3.5 | 19.0 | 0.212 |
| Weight of neonates (g) | 6.3 ± 0.4 | 6.2 ± 1.0 | 6.6 ± 0.2 | 6.1 ± 0.2 | 6.9 ± 0.9 | 8.2 ± 0.3 | 7.7 ± 0.4 | 7.4 ± 1.1 | 5.79 | 0.026 |
| Height of neonates (cm) | 6.5 ± 0.1 | 6.6 ± 0.4 | 6.7 ± 0.1 | 6.1 ± 0.3 | 6.6 ± 0.4 | 7.4 ± 0.3 | 6.9 ± 0.2 | 6.8 ± 0.5 | 6.33 | 0.037 |

Experimental Example 4: Evaluation of Gestation Periods of Animal Models Whose Cervices were Removed and Injured as in Example 2

After the cervices of female rats were excised as in Example 1, the animals were allowed to recover for 3 weeks and copulate with males. Thereafter, pregnancy rates and gestation periods were investigated. Particularly, after injection of lipopolysaccharide as in Example 2, gestation periods were more specifically evaluated.

Experimental Animals

This study was approved by the Ethics Committee for Animal Studies at Korea University (KUIACUC-2015-117). Forty-five 5-week-old female Sprague-Dawley rats were randomly divided into 6 groups. The animals in group A as a control group underwent no anesthesia and no surgery. The cervices of the animals in group B were completely removed in the same manner as in Example 1. 50 μg of lipopolysaccharide was injected between the first and second gestational sacs in the right uterine horn of each animal in group C in the same manner as in Comparative Example 2. The animals in group E were subjected to cervical excision and were injected with 50 μg of lipopolysaccharide in the same done using one-way analysis of variance (ANOVA) and the differences were calculated using the Tukey's test. A value of P<0.05 was considered statistically significant.

Results

The experimental results are shown in Table 4. Statistical analysis was conducted to confirm whether the gestation periods of the groups were different. As a result, preterm birth was induced when lipopolysaccharide was administered after cervical excision and lipopolysaccharide was administered without cervical excision. The gestation period was shortened when lipopolysaccharide was administered after cervical excision compared to when lipopolysaccharide was administered without cervical excision. The administration of lipopolysaccharide (Comparative Example 2) decreased the number of intrauterine gestational sacs, reduced the body weight and height of fetuses, and increased the mortality of fetuses. The cervical excision caused significant reductions in the number of intrauterine gestational sacs in the pregnant animals and the number of fetuses but did not lead to reductions in the body weight and height of fetuses.

TABLE 4

|  | A<br>Control<br>(n = 15) | B<br>Cervical excision<br>(n = 6) | C<br>LPS injection<br>(n = 14) | E<br>Cervical excision +<br>LPS injection (n = 3) | P |
|---|---|---|---|---|---|
| Body weight at the time of copulation (g) | 205.6 ± 10.3 | 220.0 ± 15.2 | 215.5 ± 10.9 | 226.3 ± 0.8 | 0.296 |
| Gestation period (day) | 19.5 ± 0.6 | 19.0 ± 1.0 | 18.2 ± 1.6 | 17.0 ± 0 | 0.034 |
| Number of neonates | 13.3 ± 1.6 | 9.7 ± 4.6 | 10.6 ± 3.8 | 4.0 ± 2.0 | <0.001 |
| Number of gestational sacs in the left uterine horn | 11.4 ± 3.9 | 7.3 ± 3.6 | 9.4 ± 3.0 | 4.0 ± 2.0 | 0.031 |
| Number of right gestational sacs in the right uterine horn | 7.9 ± 1.6 | 4.3 ± 1.9 | 6.7 ± 1.8 | 2.0 ± 2.0 | <0.001 |
| Weight of neonates (g) | 3.5 ± 2.9 | 3.8 ± 2.4 | 4.5 ± 2.7 | 1.3 ± 2.0 | 0.823 |
| Height of neonates (cm) | 3.4 ± 3.0 | 4.6 ± 2.9 | 4.6 ± 2.3 | 1.7 ± 2.0 | 0.0809 |

Experimental Example 5: Evaluation of Gestation Periods Depending on Extent of Cervical Excision In this experiment, the parturition times of animal models depending on the extent of cervical excision (0-100%) were measured. Specifically, 5-week-old female C57BL/6 rats were randomly grouped, 5 animals per group. The animals in group A as a control group underwent no anesthesia and no surgery. A portion (½, 50%) of the cervix of each animal in group B was removed by vaginal operation. The cervix of each animal in group C was completely removed by vaginal operation. 21 days after cervical excision, the animals were allowed to copulate with males and wait until pregnancy has been confirmed. The day when a mucus plug was found at the entrance of the vagina after copulation was regarded as day 1 of gestation and the waiting period until parturition was calculated to determine the gestation period. The results are shown in Table 5. The gestation periods of the groups were compared by statistical methods.

Cervical Excision (Vaginal Operation)

The cervical excision of Example 1 was performed under inhalation anesthesia with 2-4% isoflurane in accordance with a previous method. The protruding cervices were excised through the vaginas.

Results

The control group and the experimental groups showed no statistically significant differences in gestation period irrespective of the extent of cervical excision.

TABLE 5

|  | Control | Partially excised cervix (1/2) | Totally excised cervix | P |
|---|---|---|---|---|
| Gestation period (day) | 19.5 ± 0.6 | 20.3 ± 0.5 | 19.9 ± 0.7 | 0.089 |

Experimental Example 6: Comparison of Characteristics of the Cervices of Animal Models Having Undergone Cervical Loss and Injury Before and After Parturition 5-week-old female Sprague-Dawley or C57BL/6 rats were acclimatized to the laboratory environment for one week prior to cervical excision. After surgery, the animals were allowed to recover for 3 weeks. Then, the animals were allowed to copulate with males. 15 and 19 days after gestation and immediately after parturition, the cervices were excised and their characteristics were compared.

Experimental Animals

This study was approved by the Ethics Committee for Animal Studies at Korea University (KUIACUC-2015-117). 5-week-old female Sprague-Dawley or C57BL/6 rats were randomly divided into 4 groups. The animals in group A as a control group underwent no anesthesia and no surgery. The cervices of the animals in group B were completely removed in the same manner as in Example 1. 50 µg of lipopolysaccharide was injected between the first and second gestational sacs in the right uterine horn of each animal in group C in the same manner as in Comparative Example 2. The animals in group D were subjected to cervical excision and were injected with 50 µg of lipopolysaccharide in the same manner as in Example 2. 21 days after surgery, the animals were allowed to copulate with males and wait until pregnancy has been confirmed. In this experiment, pregnancy rates depending on the recovery period after cervical excision were investigated. As a result, the pregnancy rate decreased considerably when the recovery period was as short as 1-2 weeks and no substantial difference in pregnancy rate was found when the recovery period was ≥3 weeks. Thus, a minimum of 21 days was allowed for recovery. This experiment was designed as shown in Table 6 such that the difference in cervical changes between the control group and the experimental groups during gestation and after parturition were observed. LPS was injected at day 16 of gestation.

TABLE 6

|  | Group A, control | Group B, cervix excision | Group C, LPS injection | Group D, cervix excision + LPS injection |
|---|---|---|---|---|
| Day 15 | 3 | 3 | — | — |
| Day 19 | 3 | 3 | 3 | 3 |
| Immediately after parturition | 3 | 3 | 3 | 3 |

Cervical Excision

Cervical excision was performed and inhalation anesthesia was performed with isoflurane.

H&E Histochemical Staining for Cervical Length Observation

Figure 5B:
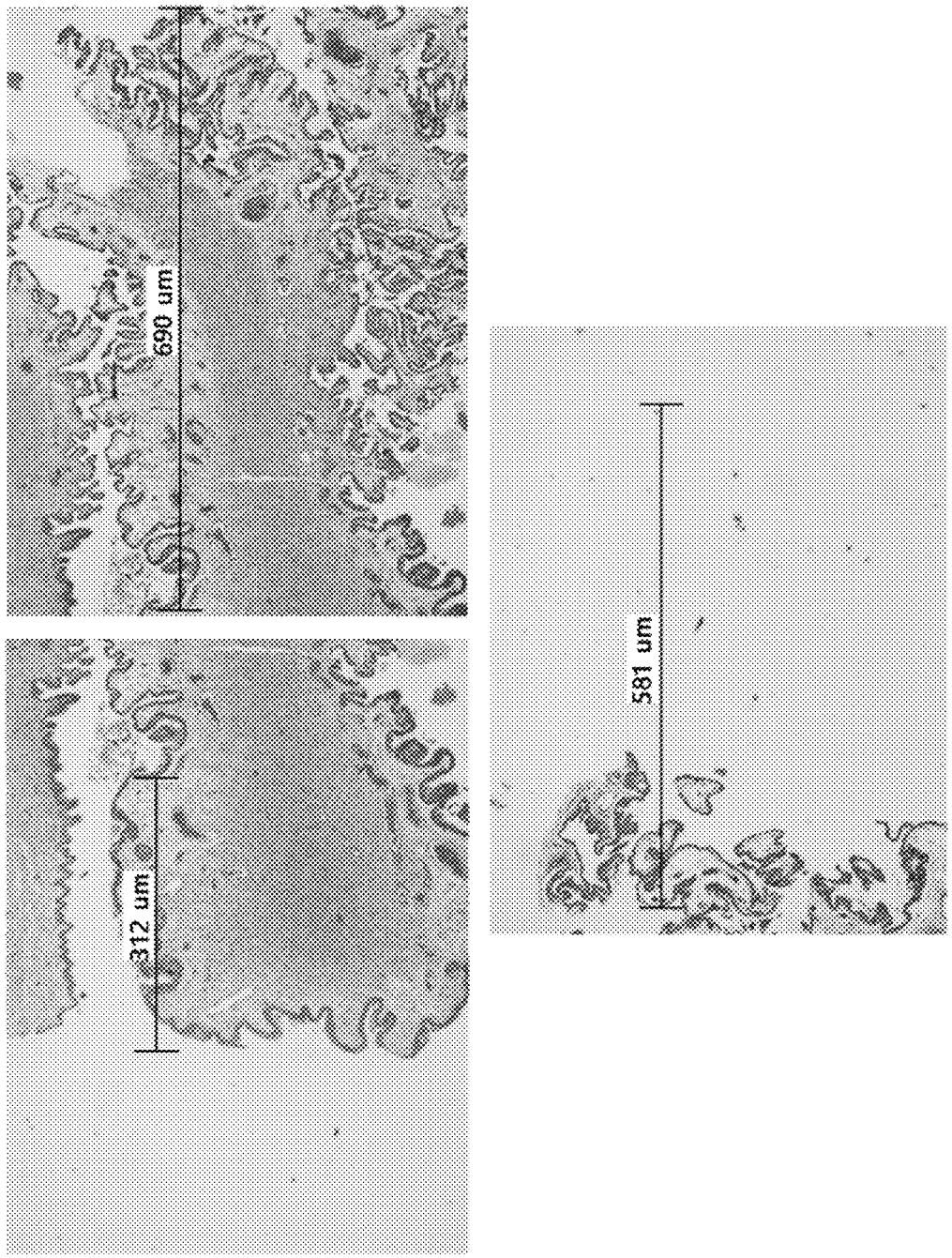

Three sections per sample were used for quantitative analysis after H&E staining. Three regions per section were randomly selected, and the cervical lengths were measured using a microscope at a magnification of 200× and averaged. FIGS. 5a and 5b are images showing the lengths of the cervices of the animals in the group having received no cervical excision and the animals in the group having received cervical excision, respectively.

Histochemical Staining with Masson's Trichrome for Muscle-Collagen Ratio Measurement Three sections per sample were used for quantitative analysis after staining with Masson's trichrome, as shown in FIGS. 6a and 6b. Three regions per section were randomly selected and the areas (smm) of the stained muscle and collagen sites were measured to calculate the muscle-collagen ratios.

Results

The results are summarized in Tables 7-10. As expected, the lengths of the cervices in the pregnant groups having undergone cervical excision were short at the time of sampling, which were statistically significant compared to those in the control group. The groups administered LPS after cervical excision also showed statistically significant results compared to the control group. The cervical lengths measured at day 15 and day 19 of gestation and after parturition were compared. As a result, there were no significant differences in cervical length between the groups at day 15 and day 19 of gestation but significant changes were observed after parturition. There were no significant differences in the weight of the cervices removed by cervical excision. The muscle-collagen ratios in the proximal, intermediate, and distal portions of the cervices before and after gestation were compared. Interestingly, the muscle-collagen ratios in the distal portions of the cervices in the LPS-administered groups were found to be low. However, no changes were observed in muscle-collagen ratio between the groups having undergone cervical excision and the control group (Tables 7-10). Table 7 shows histological examination results of the cervices excised from the groups immediately after parturition.

TABLE 9

| | B: Cervical excision (n = 6) | | | |
| --- | --- | --- | --- | --- |
| | At day 15 of gestation | At day 19 of gestation | Postpartum | P |
| Length of cervix (μm) | 1398 | 2111 | 1226.5 ± 369.8 | 0.452 |
| Muscle-collagen ratio (proximal portion) (%) | 0.6 | 1.6 | 0.5 ± 0.3 | 0.269 |
| Muscle-collagen ratio (intermediate portion) (%) | 1.1 | 1.1 | 0.4 ± 0.2 | 0.21 |
| Muscle-collagen ratio (distal portion) (%) | 0.5 | 1.2 | 0.5 ± 0.3 | 0.455 |

TABLE 10

| | C: LPS (n = 14) | | |
| --- | --- | --- | --- |
| | At day 19 of gestation | Postpartum | P |
| Length of cervix (μm) | 2381.8 ± 545.2 | 2417.3 ± 518.5 | 0.655 |
| Muscle-collagen ratio (proximal portion) (%) | 0.8 ± 0.5 | 0.4 ± 0.1 | 0.062 |
| Muscle-collagen ratio (intermediate portion) (%) | 0.6 ± 0.2 | 0.4 ± 0.1 | 0.062 |
| Muscle-collagen ratio (distal portion) (%) | 0.6 ± 0.2 | 0.4 ± 0.1 | 0.022 |

TABLE 7

| | Group A, control (n = 15) | Group B, cervix excision (n = 6) | Group C, LPS (n = 14) | Group E, cervix excision + LPS (n = 3) | P |
| --- | --- | --- | --- | --- | --- |
| Body weight at the time of copulation (g) | 205.6 ± 10.3 | 220.0 ± 15.2 | 215.5 ± 10.9 | 226.3 ± 0.8 | 0.296 |
| Weight of excised cervix (μg) | — | 13.3 ± 5.2 | — | 16.7 ± 5.8 | 0.092 |
| Length of cervix (μm) | 2110 ± 582.4 | 1490.5 ± 472.5 | 2454.8 ± 513.0 | 1876.0 ± 503.0 | 0.004 |
| Muscle-collagen ratio (proximal portion) (%) | 0.9 ± 0.5 | 0.8 ± 0.6 | 0.6 ± 0.3 | 1.3 ± 0.6 | 0.037 |
| Muscle-collagen ratio (intermediate portion) (%) | 0.9 ± 0.7 | 0.7 ± 0.4 | 0.5 ± 0.2 | 1.0 ± 0.7 | 0.229 |
| Muscle-collagen ratio (distal portion) (%) | 0.8 ± 0.5 | 0.7 ± 0.4 | 0.4 ± 0.2 | 1.1 ± 0.6 | 0.269 |

TABLE 8

| | A: Control (n = 15) | | | |
| --- | --- | --- | --- | --- |
| | At day 15 of gestation | At day 19 of gestation | Postpartum | P |
| Length of cervix (μm) | 1647.0 ± 475.5 | 1923 ± 620.5 | 2508.9 ± 347.4 | 0.028 |
| Muscle-collagen ratio (proximal portion) (%) | 1.0 ± 0.5 | 1.1 ± 0.6 | 0.8 ± 0.4 | 0.446 |
| Muscle-collagen ratio (intermediate portion) (%) | 1.0 ± 0.3 | 0.9 ± 0.4 | 0.8 ± 1.0 | 0.93 |
| Muscle-collagen ratio (distal portion) (%) | 0.8 ± 0.3 | 0.9 ± 0.7 | 0.6 ± 0.6 | 0.64 |

Experimental Example 7: Comparison of
Extracellular Matrix and Inflammatory
Characteristics of the Cervices after Gestation and
Parturition of Animal Models Having Undergone
Cervical Loss and Injury as in Example 2

5-week-old female Sprague-Dawley or C57BL/6 rats were acclimatized to the laboratory environment for one week prior to cervical excision. After surgery, the animals were allowed to recover for 3 weeks. Then, the animals were allowed to copulate with males. 19 days after gestation and immediately after parturition, the cervices were excised and their characteristics were compared.

Experimental Animals

This study was approved by the Ethics Committee for Animal Studies at Korea University (KUIACUC-2015-117). 5-week-old female Sprague-Dawley or C57BL/6 rats were randomly divided into 4 groups. The animals in group A as a control group underwent no anesthesia and no surgery. The cervices of the animals in group B were completely removed in the same manner as in Example 1. 50 μg of lipopolysaccharide was injected between the first and second gestational sacs in the right uterine horn of each animal in group C in the same manner as in Comparative Example 2. The animals in group D were subjected to cervical excision and were injected with 50 μg of lipopolysaccharide in the same manner as in Example 2. 21 days after surgery, the animals were allowed to copulate with males and wait until pregnancy has been confirmed. In this experiment, pregnancy rates depending on the recovery period after cervical excision were investigated. As a result, the pregnancy rate decreased considerably when the recovery period was as short as 1-2 weeks and no substantial difference in pregnancy rate was found when the recovery period was ≥3 weeks. Thus, a minimum of 21 days was allowed for recovery. This experiment was designed as shown in Table 11 such that the difference in cervical changes between the control group and the experimental groups during gestation and after parturition were observed.

TABLE 11

|  | Group A, control | Group B, cervix excision | Group C, LPS injection | Group D, cervix excision + LPS injection |
| --- | --- | --- | --- | --- |
| At day 19 | 6 | 6 | 6 | 6 |
| Immediately after parturition | 6 | 6 | 6 | 6 |

Cervical Excision

Cervical excision was performed and inhalation anesthesia was performed with isoflurane.

Observation of Extracellular Matrix, Inflammation, and Endocrinological Changes

The expressions of Col2A1, ADAMTS4, C3, Itgam, and CD34 were observed by q-PCR and Western blotting.

Results

The results are shown in FIGS. 7a and 7b. For C3, increases in RNA and protein expression were observed in the group having undergone cervical excision (see lane 5 in FIG. 7a) and an increase in RNA expression and a decrease in protein expression were observed in the lipopolysaccharide-administered group (see lanes 6 and 7 in FIG. 7a) at day 19 of gestation. For Col2, an increase in RNA expression and a decrease in protein expression were observed in the group having undergone cervical excision (see lane 5 in FIG. 7a) and increases in RNA and protein expression were observed in the lipopolysaccharide-administered group (see lanes 6 and 7 in FIG. 7a) at day 19 of gestation.

For ADAMTS4, increases in RNA and protein expression were observed in the group having undergone cervical excision (see lane in FIG. 7b) after parturition, an increase in RNA expression and a decrease in protein expression were observed in the lipopolysaccharide-administered group (see lanes 6-10 in FIG. 7b) after parturition, and increases in RNA and protein expression were observed in the group administered lipopolysaccharide after cervical excision (see lane 5 in FIG. 7b) after parturition. For CD11b (Itgam), increases in RNA and protein expression were observed in the group having undergone cervical excision (see lane 4 in FIG. 7b), an increase in RNA expression and a decrease in protein expression were observed in the lipopolysaccharide-administered group (see lanes 6-10 in FIG. 7b), and an increase in RNA expression and a decrease in protein expression were observed in the group administered lipopolysaccharide after cervical excision (see lane 5 in FIG. 7b). For CD34, an increase in RNA expression was observed in the group having undergone cervical excision, an increase in RNA expression was observed in the lipopolysaccharide-administered group, and an increase in RNA expression was observed in the group administered lipopolysaccharide after cervical excision. However, no protein expression was detected.

Experimental Example 8: Measurement of Waiting
Periods Until Parturition after Cervical Excision
and Subsequent Intrauterine Injection of
Lipopolysaccharide In this experiment, the waiting periods of animal models injected with lipopolysaccharide after cervical excision until parturition were measured and compared. Generally, rodents give birth to their young at day 20-23 of gestation. Thus, parturition before day 20-23 of gestation is defined as preterm birth and can be considered a significant result.

Experimental Animals

This study was approved by the Ethics Committee for Animal Studies at Korea University (KUIACUC-2014-161). Forty 10-week-old female Sprague-Dawley rats were randomly divided into 4 groups, 5 animals per group. The abdomens of the animals in group A as a control group were cut open and their abdominal walls were reclosed without any surgical operation. The cervices of the animals in group B were completely removed. 50 μg of lipopolysaccharide was injected between the first and second gestational sacs in the right uterine horn of each animal in group C in the same manner as in Comparative Example 2. The animals in group D were subjected to cervical excision and were injected with 50 μg of lipopolysaccharide in the same manner as in Example 2. 21 days after surgery, the animals were allowed to copulate with males and wait until pregnancy has been confirmed. The periods from gestation to parturition were measured. The results are shown in FIG. 8. LPS was injected at day 16 of gestation.

Gestation Period Measurement

The day when a plug was found at the entrance of the vagina after copulation was regarded as day 1 of gestation and the waiting period until parturition was calculated.

Cervical Excision

Cervical excision was performed as shown in FIG. 3 in accordance with the procedure described in Experimental Example 5 and inhalation anesthesia was performed with isoflurane.

Results

The results are shown in FIG. 8. As can be seen from FIG. 8, all animals in group D gave birth to their young within 24 h after injection of lipopolysaccharide at day 16, unlike the animals in the other groups.

Experimental Example 9: Evaluation of Gestation Periods Depending on the Dose of Lipopolysaccharide Injected after Cervical Excision Five-week-old female C57BL/6 rats were randomly divided into 3 groups, 5 animals per group. Physiological saline was injected between the first and second gestational sacs in the right uterine horn of each animal in group A, 50 μg of lipopolysaccharide was injected into each of the animals in group B having undergone cervical excision, and 100 μg of lipopolysaccharide was injected into each of the animals in group C having undergone cervical excision. 21 days after cervical excision, the animals were allowed to copulate with males and wait until pregnancy has been confirmed.

The day when a mucus plug was found at the entrance of the vagina after copulation was regarded as day 1 of gestation and the waiting period until parturition was calculated to determine the gestation period. The gestation periods of the groups were compared by statistical methods.

Results

The differences in gestation period are shown in Table 12. As shown in Table 12, the gestation period of the animals in the group administered 100 μg of LPS after cervical excision was significantly low compared to that of the animals in the control group. The gestation period of the animals in the group administered 50 μg of LPS after cervical excision tended to decrease but the difference was not statistically significant and varied depending on the individuals.

Further, when cervical excision was performed in combination with the administration of ≥200 μg of LPS, the stillbirth rate of fetuses and the miscarriage rate of pregnant animals were high, making it difficult to statistically analyze the results. When ≥500 μg of LPS was administered, it was impossible to measure results.

TABLE 12

|  | A: Control (n = 5) | B: Cervical excision (100%) + LPS 50 μg | C: Cervical excision (100%) + LPS 100 μg | P |
|---|---|---|---|---|
| Gestation period (day) | 19.3 ± 0.5 | 17.3 ± 1.6 | 16.4 ± 0.5 | 0.022 |

Although the present invention has been described herein with reference to its preferred embodiments, these embodiments do not serve to limit the invention. It should be understood that various modifications are possible without departing from the scope and spirit of the invention and such modifications are encompassed within the scope of the appended claims.

The invention claimed is:

1. A method for producing a model of preterm birth in a mammal, comprising 1) excising the cervix of the mammal through the vagina of the mammal, 2) allowing the mammal to recover, 3) making the mammal pregnant, and 4) injecting lipopolysaccharide (LPS) intrauterinely or intraperitoneally into the mammal;
   wherein the mammal is a rodent, wherein the model of preterm birth is a rodent corresponding to the mammal used;
   wherein the lipopolysaccharide is injected between the first and second gestational sacs in the distal portion of the uterus; and
   wherein the lipopolysaccharide is injected in an amount of 20 to 500 μg per mammal.

2. The method according to claim 1, wherein, in step 1), 30 to 100% of the cervix is excised.

3. The method according to claim 1, wherein the lipopolysaccharide is injected when 65 to 80% of the total gestation period passes.

4. The method according to claim 3, wherein the mammal gives birth to its young within 10 to 30 hours after injection of the lipopolysaccharide.

5. The method according to claim 1, wherein, in step 2), the mammal is recovered for 5 to 30 days.

6. A model of preterm birth in a mammal produced by the method according to claim 1, wherein the model of preterm birth is a rodent model.

7. The model of preterm birth in a mammal according to claim 6, wherein the model gives birth to its young within 10 to 30 hours after injection of the lipopolysaccharide.

8. A premature neonate born from the model of preterm birth according to claim 6.

9. The model of preterm birth in a mammal of claim 6, wherein, in step 1), 30 to 100% of the cervix is excised.

10. The model of preterm birth in a mammal of claim 6, wherein the lipopolysaccharide is injected when 65 to 80% of the total gestation period passes.

11. The model of preterm birth in a mammal of claim 10, wherein the mammal gives birth to its young within 10 to 30 hours after injection of the lipopolysaccharide.

12. The model of preterm birth in a mammal of claim 6, wherein, in step 2), the mammal is recovered for 5 to 30 days.

13. A method for producing model of preterm birth in a mammal, comprising 1) excising the cervix of the mammal through the vagina of the mammal, 2) allowing the mammal to recover, 3) making the mammal pregnant, and 4) injecting lipopolysaccharide (LPS) intrauterinely or intraperitoneally into the mammal;
   wherein the mammal is a rodent, wherein the model of preterm birth is a rodent corresponding to the mammal used;
   wherein the lipopolysaccharide is injected between the first and second gestational sacs in the distal portion of the uterus; and
   wherein the lipopolysaccharide is injected in an amount of 50 to 500 μg per mammal.

* * * * *